US009989498B2

(12) United States Patent
Lanza di Scalea et al.

(10) Patent No.: US 9,989,498 B2
(45) Date of Patent: Jun. 5, 2018

(54) NONLINEAR ULTRASONIC TESTING FOR NON-DESTRUCTIVE MEASUREMENT OF LONGITUDINAL THERMAL STRESSES IN SOLIDS

(71) Applicant: The Regents of the University of California, Oakland, CA (US)

(72) Inventors: Francesco Lanza di Scalea, San Diego, CA (US); Claudio Nucera, San Diego, CA (US)

(73) Assignee: The Regents Of The University of California, Oakland, CA (US)

( * ) Notice: Subject to any disclaimer, the term of this patent is extended or adjusted under 35 U.S.C. 154(b) by 287 days.

(21) Appl. No.: 14/766,219

(22) PCT Filed: Feb. 5, 2014

(86) PCT No.: PCT/US2014/014945
§ 371 (c)(1),
(2) Date: Aug. 6, 2015

(87) PCT Pub. No.: WO2014/124050
PCT Pub. Date: Aug. 14, 2014

(65) Prior Publication Data
US 2015/0377836 A1    Dec. 31, 2015

Related U.S. Application Data

(60) Provisional application No. 61/761,601, filed on Feb. 6, 2013.

(51) Int. Cl.
G06F 19/00    (2018.01)
G01N 29/07    (2006.01)
(Continued)

(52) U.S. Cl.
CPC .......... G01N 29/07 (2013.01); G01M 5/0025 (2013.01); G01M 5/0041 (2013.01);
(Continued)

(58) Field of Classification Search
CPC .... G01S 11/16; G06F 3/0433; G06F 3/03545; G01N 29/07
(Continued)

(56) References Cited

U.S. PATENT DOCUMENTS 2,949,028 A    8/1960    Joy
4,165,648 A    8/1979    Pagano
(Continued)

FOREIGN PATENT DOCUMENTS

WO    WO-2010036934 A2    4/2010

OTHER PUBLICATIONS

Barnett, V., et al., "Outliers in Statistical Data," 3rd Edition, Wiley, New York (1994).
(Continued)

*Primary Examiner* — Edward Raymond
(74) *Attorney, Agent, or Firm* — Mintz Levin Cohn Ferris Glovsky and Popeo, P.C.

(57) ABSTRACT

Methods and apparatus, including computer program products, are provided for nonlinear ultrasonic testing. In one aspect there is provided a method, which may include generating at least one ultrasonic wave to enable the at least one ultrasonic wave to propagate through a solid; detecting the at least one ultrasonic wave propagating through the solid; and determining a stress of the solid based on at least one of an imaginary component of a wavenumber, a wave amplitude, a wave strength, a statistical moment in a time domain, or a statistical moment in a frequency domain of the at least one ultrasonic wave.

9 Claims, 11 Drawing Sheets

(51) Int. Cl.
  *G01N 29/11* (2006.01)
  *G01N 29/46* (2006.01)
  *G01M 5/00* (2006.01)

(52) U.S. Cl.
  CPC ........... *G01M 5/0066* (2013.01); *G01N 29/11* (2013.01); *G01N 29/46* (2013.01); *G01N 2291/02491* (2013.01); *G01N 2291/02827* (2013.01); *G01N 2291/0423* (2013.01); *G01N 2291/0425* (2013.01); *G01N 2291/2623* (2013.01); *G01N 2291/2634* (2013.01)

(58) Field of Classification Search
  USPC .................................. 702/42, 182–185, 188
  See application file for complete search history.

(56) References Cited

U.S. PATENT DOCUMENTS

| | | |
|---|---|---|
| 5,038,787 A | 8/1991 | Antich et al. |
| 5,386,727 A | 2/1995 | Searle |
| 5,777,891 A | 7/1998 | Pagano et al. |
| 6,055,862 A | 5/2000 | Martens |
| 6,186,004 B1 | 2/2001 | Kaduchak et al. |
| 6,324,912 B1 | 12/2001 | Wooh |
| 6,401,044 B1 | 6/2002 | Ibanez Rodriguez et al. |
| 6,570,497 B2 | 5/2003 | Puckette, IV et al. |
| 6,715,354 B2 | 4/2004 | Wooh |
| 7,082,833 B2 | 8/2006 | Heyman et al. |
| 7,263,886 B2 | 9/2007 | Jury |
| 7,389,694 B1 | 6/2008 | Hay et al. |
| 7,882,742 B1 | 2/2011 | Martens |
| 7,942,058 B2 | 5/2011 | Turner |
| 8,020,446 B2 | 9/2011 | Bestebreurtje |
| 8,176,786 B2 | 5/2012 | Sohn et al. |
| 8,626,459 B2 | 1/2014 | Di Scalea et al. |
| 9,010,186 B2 | 4/2015 | Pagano |
| 2004/0003662 A1 | 1/2004 | Kenderian et al. |
| 2005/0072236 A1 | 4/2005 | Heyman et al. |
| 2006/0059992 A1 | 3/2006 | Jury |
| 2006/0137451 A1 | 6/2006 | Dewangan et al. |
| 2006/0201253 A1 | 9/2006 | Gonzales et al. |
| 2007/0214892 A1 | 9/2007 | Turner et al. |
| 2008/0201089 A1 | 8/2008 | Diaz et al. |
| 2008/0223137 A1 | 9/2008 | Bestebreurtje |
| 2009/0056454 A1 | 3/2009 | Turner |
| 2009/0301198 A1 | 12/2009 | Sohn et al. |
| 2010/0024559 A1 | 2/2010 | Bossi et al. |
| 2011/0238336 A1 | 9/2011 | Di Scalea et al. |
| 2016/0304104 A1 | 10/2016 | Witte et al. |
| 2016/0305915 A1 | 10/2016 | Witte et al. |

OTHER PUBLICATIONS

Bartoli, Ivan, et al., "Stress Dependence of ultrasonic guided waves in rails," Transportation Research Record: Journal of the Transportation Research Board 2159 (2010): 91-97.

Chen, Feng, and Paul D. Wilcox. "The effect of load on guided wave propagation." Ultrasonics 47.1 (2007): 111-122.

Damljanovic, Vesna, and Richard L. Weaver. "Forced response of a cylindrical waveguide with simulation of the wavenumber extraction problem." The Journal of the Acoustical Society of America 115.4 (2004): 1582-1591.

Egle, D. M., and D. E. Bray. "Measurement of acoustoelastic and third?order elastic constants for rail steel." The journal of the Acoustical Society of America 60.3 (1976): 741-744.

Gonzalez, R.C., et al., "Digital Image Processing," 3rd Edition, Prentice-Hall, Inc., Upper Saddle River, NJ (2006).

Ibarra-Castanedo, C., et al., "Comparative Study of Active Thermography Techniques for the Nondestructive Evaluation of Honeycomb Structures," Research in Nondestructive Evaluation 20:1-31 (2009).

Ibarra-Castanedo, C., et al., "Qualitative and Quantitative Assessment of Aerospace Structures by Pulsed Thermography," Nondestructive Testing and Evaluation 22 (2-3): 199-215 (2007).

Kerr, Arnold D. "Lateral buckling of railroad tracks due to constrained thermal expansions—a critical survey." Proc. Symp. Railroad Track Mechanics (Princeton University, New Jersey, USA, 1975). Ed. A. D. Kerr. 1978.

Kerr, Arnold D. Thermal Buckling of Straight Tracks: Fundamentals, Analyses, and Preventive Measures. No. FRA/ORD-78/49 Intrm Rpt.. 1978.

Kish, A., and D. Clark. "Better management of CWR neutral temperature through more efficient distressing." Proceedings of 2004 AREMA Conference, May 2004.

Loveday, Philip W. "Semi-analytical finite element analysis of elastic waveguides subjected to axial loads." Ultrasonics 49.3 (2009): 298-300.

Maldaque, X.P.V., et al., "Pulse Phase Infrared Thermography," Journal of Applied Physics 79 (5):2694-2698 (1996).

Mallat, S.G., "A Theory for Multiresolution Signal Decomposition: The Wavelet Representation," IEEE Transactions on Pattern Analysis and Machine Intelligence 11 (7):674-693 (1989).

Pilla, M., et al., "New Absolute Contrast for Pulsed Thermography," Quantitative Infrared Thermography 53-58 (2002).

Read, D. "Evaluation of the MAPS-SFT rail neutral temperature measurement technique." Technology Digest TD-10-002, Transportation Technology Center, Inc (2010).

Read, David, and Andrew Kish. "Automation of Rail Neutral Temperature Readjustment Methodology for Improved CWR Performance." Railway Track and Structures 104.5 (2008).

Read, David, and Bill Shust. "Investigation of prototype rail neutral temperature measurement system." Railway Track and Structures 103.6 (2007).

Rizzo, P., et al., "Unsupervised Learning Algorithm for Fatigue Crack Detection in Waveguides," Smart Materials and Structures 18:025016 (2009).

Rizzo, P., et al., "Wavlet-Based Unsupervised and Supervised Learning Algorithms for Ultrasonic Structural Monitoring of Waveguides," Reece, P.L. (ed), Progress in Smart Material and Structures Research, NOVA Publishers, pp. 227-290 (2007).

Rose, Joseph L., et al. "Guided wave inspection potential of defects in rail." NDT & E International 37.2 (2004): 153-161.

Shepard, S.M., "Advances in Pulsed Thermography," Thermosense XXIII 4360 (1): 511-515 (2001).

Shepard, S.M., et al., "Reconstruction and Enhancement of Active Thermographic Image Sequences," Optical Engineering 42 (5): 1337-1342 (2003).

Strang, G., et al., "Wavelets and Filter Banks," Wellesley College, Wellesley (1996).

Sun, J.G., "Analysis of Pulsed Thermography Methods for Defect Depth Prediction," Journal of Heat Transfer 128:329-338 (2006).

Wilcox, P., et al. "Guided wave testing of rail." Insight-Non-Destructive Testing and Condition Monitoring 45.6 (2003): 413-420.

NONLINEAR ULTRASONIC TESTING FOR NON-DESTRUCTIVE MEASUREMENT OF LONGITUDINAL THERMAL STRESSES IN SOLIDS

CROSS-REFERENCES TO RELATED APPLICATIONS

The current application is a national-phase entry of Patent Cooperation Treaty application no. PCT/US2014/014945, entitled "NONLINEAR ULTRASONIC TESTING FOR NON-DESTRUCTIVE MEASUREMENT OF LONGITUDINAL THERMAL STRESSES IN SOLIDS," which has an international filing date of Feb. 5, 2014, and which claims priority to U.S. Patent Application No. 61/761,601, entitled "NONLINEAR ULTRASONIC TESTING FOR NON-DESTRUCTIVE MEASUREMENT OF LONGITUDINAL THERMAL STRESSES IN SOLIDS," filed Feb. 6, 2013. The disclosure of this application is hereby incorporated by reference in its entirety for all purposes.

STATEMENT OF GOVERNMENT SPONSORED SUPPORT

This invention was made with government support under grant No. FR-RRD-0009-10-01-03 awarded by Federal Railroad Administration (FRA). The government has certain rights in the invention.

BACKGROUND

Today, railways typically use continuous-welded rail (CWR). In CWR, the rails are welded to form a very long, so-called "continuous" rail. In some instances, the CWR may be one or more miles in length. CWR came into use because it requires fewer joints, providing thus a smoother ride for the train and passengers. With the advent of high-speed rail, CWR allows the train to travel over the rails with less friction as there are fewer joints causing friction. CWR can also be used in passenger and freight rail transportation systems that run at low or regular speeds.

SUMMARY

Methods and apparatus, including computer program products, are provided for non-destructive testing of solids, such as rails, pipes, and the like.

In some example embodiments, there may be provided a method, which includes generating at least one ultrasonic wave to enable the at least one ultrasonic wave to propagate through a solid; detecting the at least one ultrasonic wave propagating through the solid; and determining a stress of the solid based on at least one of an imaginary component of a wavenumber, a wave amplitude, a wave strength, a statistical moment in a time domain, or a statistical moment in a frequency domain of the at least one ultrasonic wave.

In some variations, one or more of the features disclosed herein including the following features can optionally be included in any feasible combination. A neutral temperature of the solid may be determined based on at least a measurement of a temperature of the solid and an extrema value of at least one of the imaginary component of the wavenumber, the wave amplitude, the wave strength, the statistical moment in the time domain, or the statistical moment in the frequency domain of the at least one ultrasonic wave, wherein the neutral temperature of the solid represents the temperature at which a thermal stress in the solid is about zero, wherein the neutral temperature of the solid represents the temperature at which a thermal stress in the solid is about zero. The at least one of the imaginary component of the wavenumber, the wave amplitude, the wave strength, the statistical moment in the time domain, or the statistical moment in the frequency domain of the at least one ultrasonic wave may be normalized. The solid may include a rail, a pipe, or a combination thereof. The at least one ultrasonic wave may include an ultrasonic guided wave propagating along a predominant direction of a rail, a pipe, or a combination thereof. The at least one ultrasonic wave may include an ultrasonic Rayleigh wave propagating along the surface of the solid. The at least one ultrasonic wave may include an ultrasonic longitudinal wave, an ultrasonic shear wave propagating in one or more directions in the solid, or a combination thereof. The stress may include thermal stress, a tensile stress, a compressive stress, and/or a thermal stress of the solid at a neutral temperature of the solid.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

BRIEF DESCRIPTION OF THE DRAWING

These and other aspects will now be described in detail with reference to the following drawings.

Like reference symbols in the various drawings indicate like elements.

DETAILED DESCRIPTION

Figure 1:
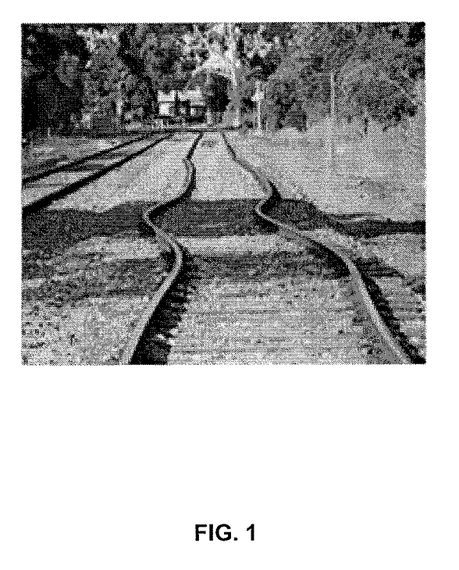
FIG. 1 depicts an example of rails buckling.

With the advent of continuous-welded rail (CWR), the rail industry has become increasingly concerned with failures caused by restrained thermal expansion and contraction. Specifically, excessive tensile loads, occurring in cold weather, may lead to rail breakage, and during warm weather, excessive compression loads may lead to rail buckling. Breakage and/or buckling, as depicted at FIG. 1, may lead to failures, which may lead to train derailments. To avoid such catastrophes, mechanisms to determine the longitudinal forces (or stresses) in the rail as a function of changing rail temperature may be used. By knowing the existence and/or location of excessive tensile loads and/or excessive compressive loads remedial actions may be taken, such as for example cutting sections of rail and/or inserting rail plugs to avoid rail breakage in cold weather or rail buckling in hot weather.

A property of a rail is the neutral temperature ($T_N$). The neutral temperature represents the rail temperature at which the thermal longitudinal force (or stress) in the rail is zero. The neutral temperature may be associated with the laying (or anchoring) temperature of a rail, but even at the rail's neutral temperature $T_N$, the rail may be in a state having residual stresses caused by at least the manufacturing of the rail. However, the neutral temperature mechanisms described herein are directed to determining the thermal stresses of the rail.

The longitudinal force, P, in a rail may be mapped to the current rail temperature, T. For example, longitudinal force, P, in a rail may be given by the following equation:

$$P = A\sigma = -\alpha EA(T - T_N) \quad \text{Equation (1)},$$

wherein

P is a thermal load generated in the rail by the constrained thermal deformation, A is the cross-sectional area of the rail, σ is the longitudinal thermal stress in the rail (e.g., also referred to as thermal stress), α is the coefficient of thermal expansion of steel, E is Young's Modulus of steel, T is the current rail temperature; and $T_N$ is the neutral temperature. As such, when the current rail temperature is equal to the neutral temperature ($T = T_N$), the resulting thermal load, P, is about zero (and the corresponding thermal stress, σ, is also about zero).

The neutral temperature, $T_N$, of the rail while in service is relatively dynamic in the sense that the neutral temperature, $T_N$, may change due to numerous factors. For example, the rail's neutral temperature may change while in service due to rail kinematics (e.g., creep, breathing, ballast settlement, and the like) and rail maintenance (e.g., installation, realignment, distressing, broken rail repairs, and the like). Even for a rail with a known laying temperature or anchoring temperature, the neutral temperature for a rail in service may not be known.

In some exemplary embodiments, the mechanisms described herein relate to determining in-situ and nondestructively the neutral temperature of a rail, $T_N$, or the rail temperature where the resulting thermal load, P, and therefore the resulting thermal stress, σ, are about zero. This information may enable remedial actions to prevent rail breakage in cold weather and rail buckling in hot weather. This information may also be useful to prevent breakage and buckling of other structures, including pipelines in the gas and oil industry.

In some exemplary embodiments, there may be provided a system, a method, and/or computer-readable medium configured to non-destructively determining the neutral temperature ($T_N$) of a CWR (or other object, pipeline, and the like) in-service by tracking the nonlinear behavior of ultrasonic waves propagating through the solid. The particular nonlinear parameter that may be tracked is, in some example embodiments, an imaginary component of the wave number, $k_{im}$, for a given ultrasonic wave mode.

Figure 2:
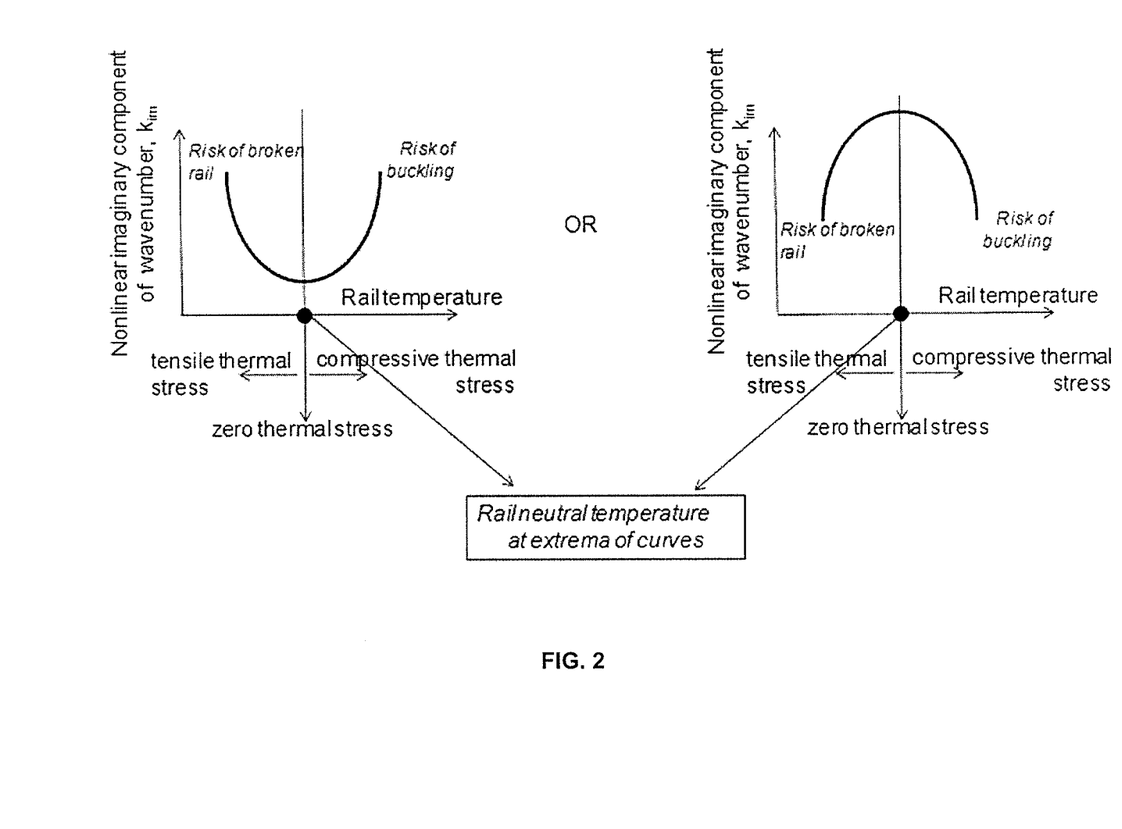
FIG. 2 depicts plots.

The imaginary component of the wave number, $k_{im}$, may be related to the wave amplitude (or strength) at a given propagation distance. The imaginary component of the wave number, $k_{im}$, may assume an extrema value (e.g., a minimum or a maximum) when the thermal load on the solid, P, or the thermal stress, σ, are about zero, e.g., when the solid's temperature, T, is at the neutral temperature $T_N$. For example, the extrema value may be a high value (or a maxima) or a low value (or a minima) of the output as a function of the solid's temperature. Therefore, by measuring the $k_{im}$ of an ultrasonic wave in the solid as a function of the temperature of the solid, T, for some period (e.g., 24 hours), the point when $T = T_N$ (for example, the solid's neutral temperature) may be identified by detecting an extrema of $k_{im}$. Examples of the extrema are shown in FIG. 2.

The measurement of $k_{im}$ may be accomplished by generating an ultrasonic wave in the solid by at least a generator, detecting the ultrasonic wave after some propagation distance by at least one detector, and measuring the wave's amplitude or strength. The measurement of the wave's amplitude or strength may be accomplished by a number of metrics, which may be calculated either in the time domain of the detected wave (e.g., peak-to-peak, root-mean-square, variance and other statistical moments of the wave) and/or calculated in the frequency domain of the detected wave (e.g., from Fast Fourier Transform amplitude spectra).

The displacement of the particles of the solid (e.g., rail, pipeline, and the like), when an elastic wave is propagating, may be described by the following expression:

$$u(x,t) = U_0 e^{-k_{im}x} e^{i(k_{re}x - 2\pi ft)} \quad \text{Equation (2)},$$

wherein u is the wave displacement in a given direction, x is the wave propagation direction, t is time, $U_0$ is the initial wave amplitude at x=0, e is Euler's number (=2.71828 . . . ), π is the pi symbol (=3.14159), f is the wave frequency, $k_{re}$ is the real component of the wave number (which is equal to 2π/wavelength), and $k_{im}$ is the imaginary component of the wave number.

Figure 3:
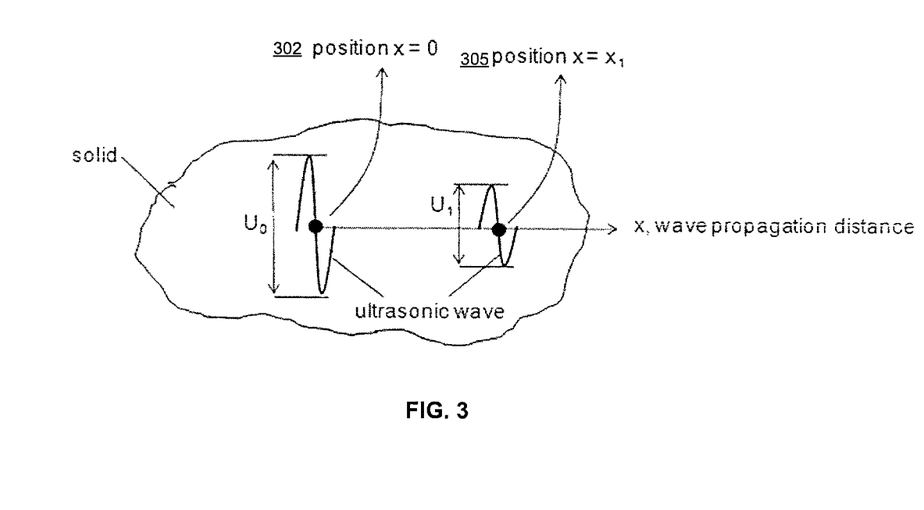
FIG. 3 depicts plots of wave amplitudes as a function of propagation distance.

According to Equation (2), the amplitude of the wave at a propagation distance of $x_1$ 305, as depicted in FIG. 3, may be given by:

$$U_1 = U_0 e^{-k_{im}x_1} \quad \text{Equation (3)},$$

wherein $U_1$ is the wave amplitude at distance $x = x_1$, and the other symbols were defined above. Therefore, the imaginary component of the wave number, $k_{im}$, may control the amplitude assumed by the wave after a given propagation distance in the solid (see, e.g., FIG. 3 as wave propagates from 302 to 305).

Due to the application of the thermal load (or thermal stress) in the constrained solid (rail or pipeline), the elastic strain energy of the solid contains terms that may be cubic as a function of strain. This may lead to a nonlinear wave equation, so the ultrasonic wave propagating through the thermally stressed solid may become nonlinear.

The nonlinear wave equation may take the following form:

$$\frac{\partial^2 u}{\partial t^2} = v^2 \left[1 - \gamma \left(\frac{\partial u}{\partial x}\right)\right] \frac{\partial^2 u}{\partial x^2}, \quad \text{Equation (4)}$$

wherein u is the wave displacement in a given direction, t is time,

∂ is the derivative symbol, x is the wave propagation direction, v is the wave velocity, and γ is a nonlinear factor.

A manifestation of the wave nonlinearity is that the imaginary component of the wave number, $k_{im}$, in Equations (2) and (3), may change as a function of thermal load (or thermal stress) for a given wave propagation frequency, f. The change in $k_{im}$ may be about the same, irrespective of the sign of the thermal load or thermal stress (i.e., the new $k_{im}$, may depend only on the absolute value of the thermal load, |P|, or absolute value of the thermal stress, |σ|). The nonlinear wave theory may indicate that the imaginary component of the wave number, $k_{im}$, may assume an extrema value (e.g., minimum or maximum) when the thermal load, or thermal stress, are about zero, i.e. when the temperature of the solid is at about the neutral temperature, $T_N$. It is the particular wave mode propagating through the solid that determines whether the $k_{im}$ assumes a minimum value and/or a maximum value at the neutral temperature condition.

Figure 4A:
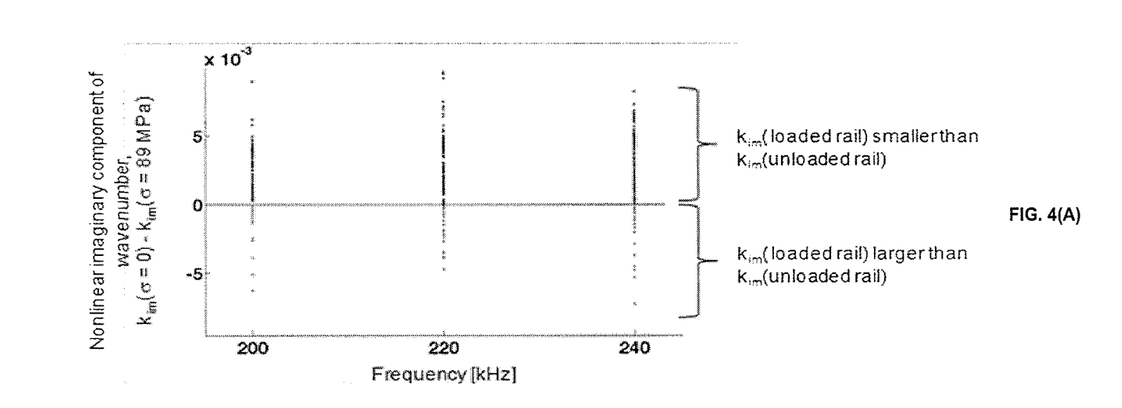
FIG. 4 depicts an example set of simulation results.

FIG. 4(A) shows a simulation analysis of ultrasonic guided wave propagation in a 136RE rail. Ultrasonic guided waves may refer to waves propagating predominantly along a running direction of the rail. There are several guided wave modes for a rail (or, e.g., a pipeline, solid, and the like). Each guided wave mode may have one nonlinear imaginary component of the wave number, $k_{im}$, at a given propagation frequency, f. Example results are shown in FIG. 4(A), which refer to two conditions of the model rail: a "loaded rail" condition (were a thermal tensile stress of 89 MPa has been applied to the rail model) and an "unloaded rail" condition (were no thermal force or thermal stress is applied, i.e. the rail model is at about neutral temperature, $T_N$). The value of $k_{im}$ may change between the loaded rail and the unloaded rail. For each wave mode at the three arbitrarily selected frequencies of 200 kHz, 220 kHz and 240 kHz, FIG. 4(A) plots the difference in $k_{im}$ between the unloaded rail and the loaded rail. Each of the dots represents a particular wave mode. It is clear that for some modes, this difference is negative (i.e., $k_{im}$ increases from the unloaded rail case to the loaded rail case), whereas for other modes this difference is positive (i.e., $k_{im}$ decreases from the unloaded rail case to the loaded rail case). Therefore, if $k_{im}$ is measured for a period of time for various rail temperatures, some wave modes may exhibit a minimum of $k_{im}$ at the neutral temperature condition, whereas other wave modes may exhibit a maximum of $k_{im}$ at the neutral temperature condition.

Figure 4B:
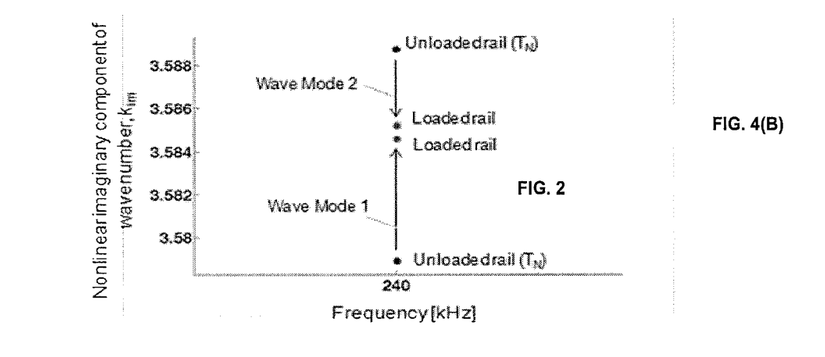

FIG. 4(B) is another representation of the same concept. FIG. 4(B) shows a zoom around two particular guided wave modes at the frequency of 240 kHz. It may be seen that while the $k_{im}$ of Wave Mode 1 increases from the unloaded rail case to the loaded rail case, the $k_{im}$ of Wave Mode 2 decreases from the unloaded rail case to the loaded rail case.

In some example implementations, the subject matter described herein may allow the measurement of a rail's neutral temperature, $T_N$, in a non-destructive manner, as noted. Moreover, in some implementations, the systems, methods, and computer-readable media described herein may determine a rail's neutral temperature, $T_N$, with an accuracy of less than about +/−5° F., although other accuracies may be realized as well. Furthermore, in some example implementations, the systems, methods, and computer-readable media described herein may determine rail thermal stresses (hence rail Neutral Temperature) with a sensitivity sufficient to minimize the effects of (a) temperature variation alone (changes in elastic constants due to temperature fluctuations), (b) steel texture variation, (c) steel residual stresses from manufacturing or wheel-rail interaction phenomena, and/or (d) support conditions including tie-to-tie variations and rail fasteners. Although the examples herein refer to rails, other objects and structures may be used as well including structures that are prone to thermal stress failures, such as pipelines in the oil and gas industry.

Referring again to FIG. 2, the subject matter disclosed herein may measure the nonlinearity of ultrasonic waves propagating in a solid (e.g., a rail, a pipeline, and the like) in terms of the imaginary component of the wave number, $k_{im}$, as a function of the solid's temperature, T. This measurement may be taken for some period, for example 24 hours. At the time when the thermal force in the solid, or the thermal stress, are about zero (neutral temperature condition), the imaginary component of the wave number, $k_{im}$, will assume an extrema value (minimum or maximum, depending on the particular wave mode that is propagated in the solid). Therefore, the solid's temperature T corresponding to the extrema value of $k_{im}$, is the solid's neutral temperature, $T_N$.

In some example implementations, a method for determining the rail (or, e.g., the pipeline or other solid/object) neutral temperature includes one or more of the following steps: generating an ultrasonic wave in the solid (rail or pipeline) by at least one generator; detecting that ultrasonic wave by at least one detector; simultaneously measuring the solid's temperature for a period of time (e.g., 24 hours or less); measuring the imaginary component of the wave number $k_{im}$ of the measured ultrasonic wave; and detecting an extrema value (minimum or maximum) of $k_{im}$ as a function of the solid's temperature: the solid's temperature corresponding to the extrema value of $k_{im}$ is the solid's neutral temperature ($T_N$).

The type of ultrasonic waves that may be used for the measurement of the neutral temperature may be at least one of the following: ultrasonic guided waves (i.e., waves propagating predominantly along a running direction of the rail or pipeline—including ultrasonic Rayleigh or surface waves), and/or ultrasonic bulk waves (i.e., longitudinal waves or shear waves propagating in any direction of the rail or pipeline).

The ultrasonic testing configurations that may be used may be one of the following: through-transmission configuration (i.e., the wave is generated at one point of the rail/pipe and it is detected at a different point of the rail/pipe) and/or pulse-echo configuration (i.e., the wave is generated at one point of the rail/pipe and it is detected at the same point after it undergoes some reflections from surfaces of the rail/pipe).

The ultrasonic wave may be generated in the solid by one of the following: a contact mechanism, including: a piezoelectric transducer, an impactor (such as a hammer), a shaker (mechanical or electromagnetic), and/or a non-contact mechanism, including: an air-coupled transducer, an electromagnetic-acoustic transducer (EMAT), or a pulsed laser. Similarly, the ultrasonic wave may be detected by one of the following: a contact mechanism, including: a piezoelectric transducer, an accelerometer, and/or a non-contact mechanism, including: an air-coupled transducer, an electro-magnetic-acoustic transducer (EMAT) or a laser interferometer. Moreover, the ultrasonic generator and detector may be implemented in one of the following systems: a stationary "wayside" system for measurements at fixed positions of the solid (rail or pipeline) or an "in-motion" system for continuous measurements at several positions (by ultrasonic wheels or sleds, for example). In some example embodiments, the wave generator may be implemented as a contact mechanism including a piezoelectric transducer, a wheel transducer, an impactor, and/or an electromagnetic or mechanical shaker. The wave generator may also be implemented as a non-contact mechanism including one of an air-coupled transducer, an electro-magnetic-acoustic transducer EMAT, and/or a pulsed laser.

Figure 5:
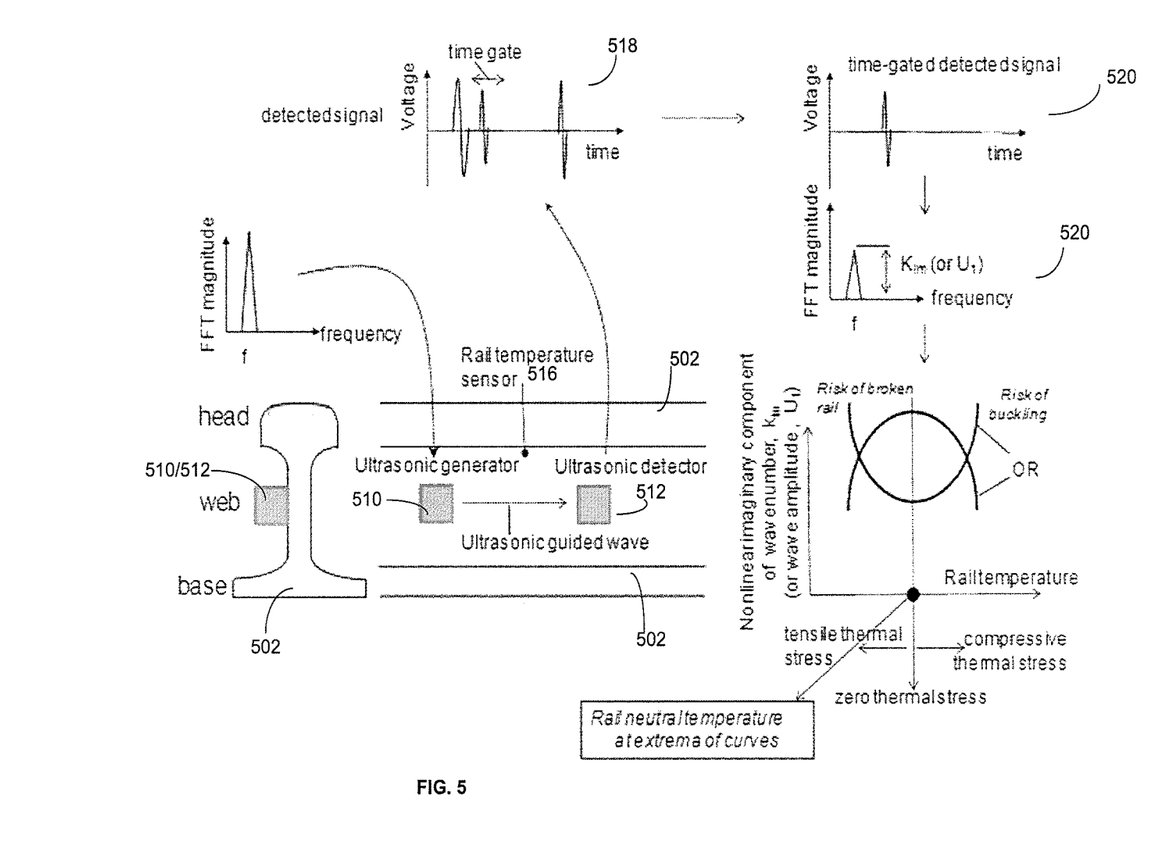
FIGS. 5 and 6 depict example systems.

In some example implementations, ultrasonic guided waves, i.e., waves propagating predominantly along a running direction of the rail, may be used. These include ultrasonic Rayleigh (or surface) waves. A schematic of a possible guided wave implementation for measuring the neutral temperature of a rail 502 is shown at FIG. 5. An ultrasonic generator 510, such as a piezoelectric transducer, although other generators are possible as noted, is attached to the rail web by way of an ultrasonic couplant (e.g., liquid or gel). The ultrasonic generator may induce in the rail ultrasonic guided waves at a specific frequency, f. The ultrasonic guided waves propagate through the rail and are detected at some distance by an ultrasonic detector 512, such as another piezoelectric transducer, although other detectors are possible as noted. The wave detector may be implemented as a contact mechanism including a piezoelectric transducer, a wheel-transducer, and/or an accelerometer. The wave detector may also be implemented as a non-contact mechanism including one of an air-coupled transducer, an electro-magnetic-acoustic transducer EMAT, a laser interferometer, and/or a laser vibrometer.

A temperature sensor 516 may also used to measure the temperature of the rail, T. The temperature sensor may be one of a thermocouple, a non-contact infrared temperature sensor, or other types of temperature sensors.

The ultrasonic signal detected by the ultrasonic detector may, in some implementations, be gated in time 518 to select a specific guided wave mode 520. The gated signal 520 may then be processed to measure the imaginary component of the wave number, $k_{im}$. The term $k_{im}$, that is related to the amplitude of the detected wave $U_1$ from Equation (3), may be measured by performing a Fast-Fourier Transform (FFT) on the gated detected signal and calculating the peak amplitude (or peak power) at the generation frequency f. Alternatively, the imaginary component of the wave number, $k_{im}$, may be measured by one or more of the following features: a) root-mean square of the amplitude of the detected portion of the waves, b) variance of the amplitude of the detected portion of the waves, c) cross-correlation value of the amplitude of the detected portion of the waves, d) peak-to-peak value of the amplitude of the detected portion of the waves, e) peak value of the amplitude of the detected portion of the waves, f) Kurtosis value (e.g., a measure of the peakedness of the source signal, where a higher Kurtosis value implies more of the variance due to infrequent extreme deviations) of the amplitude of the detected portion of the waves, g) at least one other time-domain Statistical Moment corresponding to properties of the detected portion of the waves, h) at least one other frequency-domain Statistical Moment corresponding to the properties of the detected portion of the waves, and/or i) normalized values of any of feature values.

The imaginary component of the wave number, $k_{im}$, or the detected wave amplitude, $U_1$, may then be plotted as a function of the rail's temperature, T, as measured by the temperature sensor, for a period of time (e.g., 24 hours, although different times are possible). The rail's temperature T that corresponds to an extreme value (e.g., minimum or maximum) of $k_{im}$ (or $U_1$) may be the rail's neutral temperature, $T_N$. It is the particular guided wave mode analyzed that may determine whether the $k_{im}$, assumes a minimum value or a maximum value at the neutral temperature condition, examples of which are depicted at FIGS. 4A-B.

Figure 6:
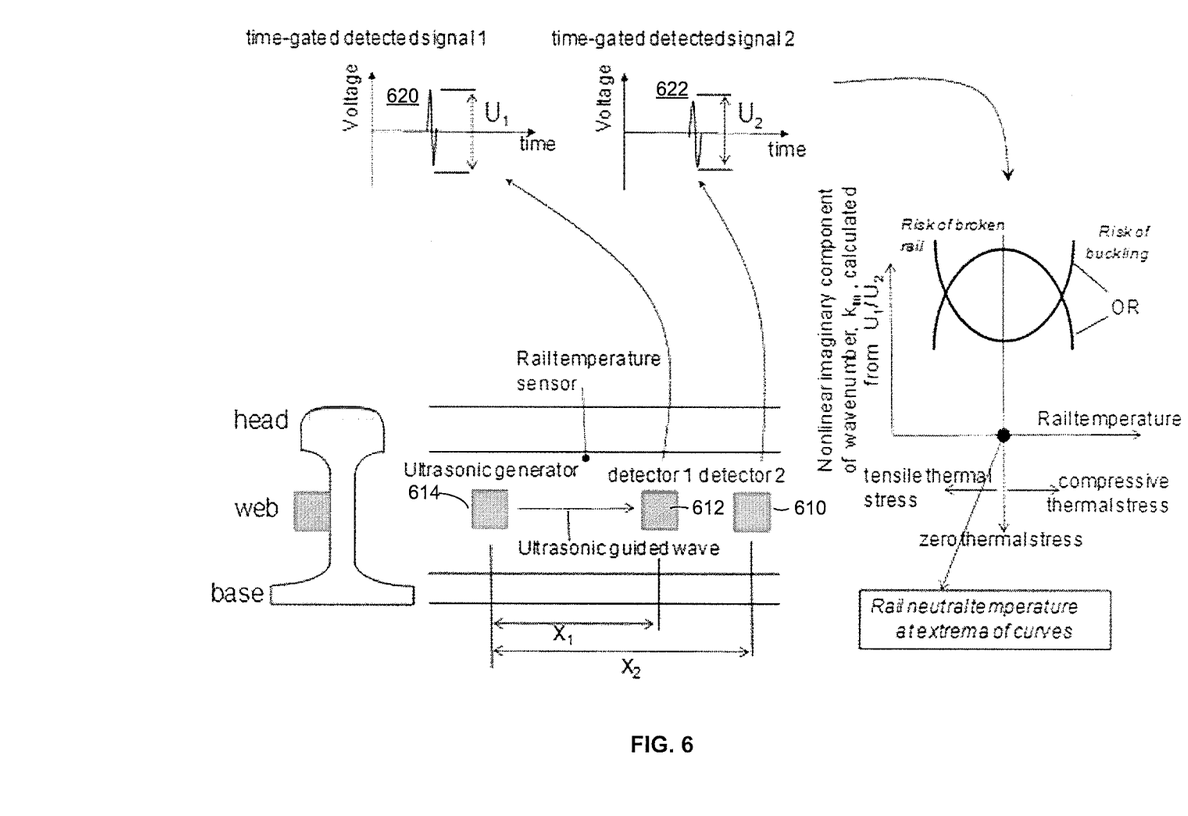

In another possible implementation of ultrasonic guided waves for the measurement of neutral temperature, two ultrasonic detectors 610-612 may be used to detect the waves generated in the rail by the ultrasonic generator 614, an example of which is shown at FIG. 6. FIG. 6 is similar to FIG. 5 in some respects but depicts the use of two ultrasonic detectors 610-612. The two ultrasonic detectors may be positioned at a distance Δx=x2−x1 from one another. Ultrasonic detector 1, at distance $x_1$ from the generator, may detect a wave with amplitude $U_1$ that may be expressed as $U_1 = U_0 e^{-k_{im} x_1}$ from Equation (3). Ultrasonic detector 2, at distance $x_2$ from the generator, may detect a wave with amplitude $U_2$ that may be expressed as $U_2 = U_0 e^{-k_{im} x_2}$. The imaginary component of the wave number, $k_{im}$, may therefore be calculated, for example, by the following expression:

$$k_{im} = \frac{1}{x_2 - x_1} \ln\left(\frac{U_1}{U_2}\right), \qquad \text{Equation (5)}$$

wherein
$k_{im}$ is the imaginary component of the wave number,
$(x_2-x_1)$ is the distance between the two detectors,
ln is the symbol for natural logarithm,
$U_1$ is the wave amplitude measured by detector 1, and
$U_2$ is the wave amplitude measured by detector 2.

As discussed above for the implementation of FIG. 5, the wave amplitudes $U_1$ and $U_2$ of Equation (5) and FIG. 6 at 620-622 may be measured by performing a FFT on the gated signals detected by the two detectors, and calculating the peak amplitude (or, e.g., peak power) of the two FFT spectra at the generation frequency f. Alternatively, the wave amplitudes $U_1$ and $U_2$ may be measured by one or more of the following features: a) root-mean square of the amplitude of the detected portion of the waves, b) variance of the amplitude of the detected portion of the waves; c) cross-correlation value of the amplitude of the detected portion of the waves, d) peak-to-peak value of the amplitude of the detected portion of the waves, e) peak value of the amplitude of the detected portion of the waves, f) Kurtosis value (e.g., a measure of the peakedness of the source signal, where a higher Kurtosis value implies more of the variance due to infrequent extreme deviations) of the amplitude of the detected portion of the waves, g) at least one other time-domain Statistical Moment corresponding to properties of the detected portion of the waves, h) at least one other frequency-domain Statistical Moment corresponding to the properties of the detected portion of the waves, and/or i) normalized values of any of feature values.

Figure 7:
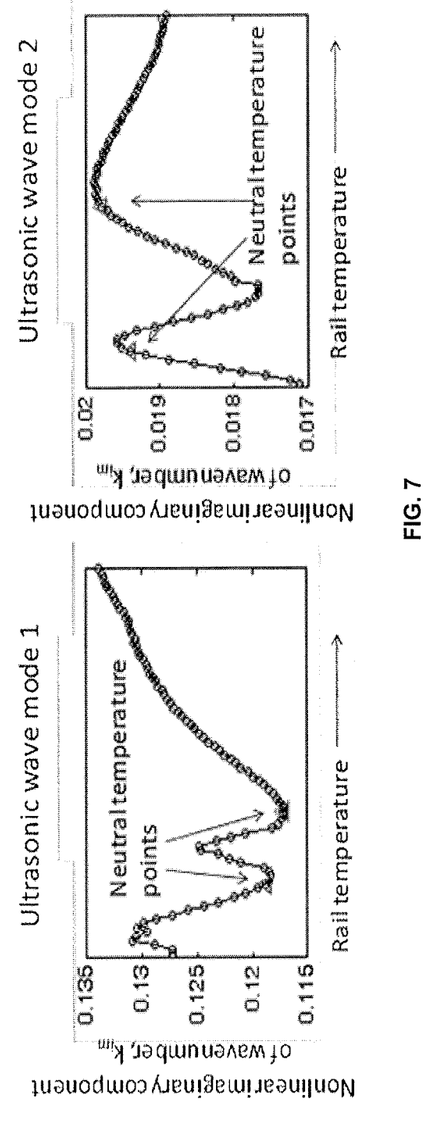
FIG. 7 depicts example simulation results.

An example of neutral temperature measurement using the ultrasonic guided wave implementation described in FIG. 5 is shown in FIG. 7. The result at FIG. 7 shows the measurement of two neutral temperature points of a 136RE rail. The rail may be heated by an electrical wire and then cooled in air. This temperature cycle made the rail cross its neutral temperature point twice. The plot on the left shows the imaginary component of the wave number, $k_{im}$, measured from the peak amplitude of the FFT magnitude spectrum on one guided wave mode (mode 1). For this first mode, the neutral temperature points correspond to minima of the $k_{im}$ curve. The plot on the right shows the same result from another guided wave mode (mode 2). For this second mode, the neutral temperature points correspond to maxima of the $k_{im}$ curve.

Figure 8:
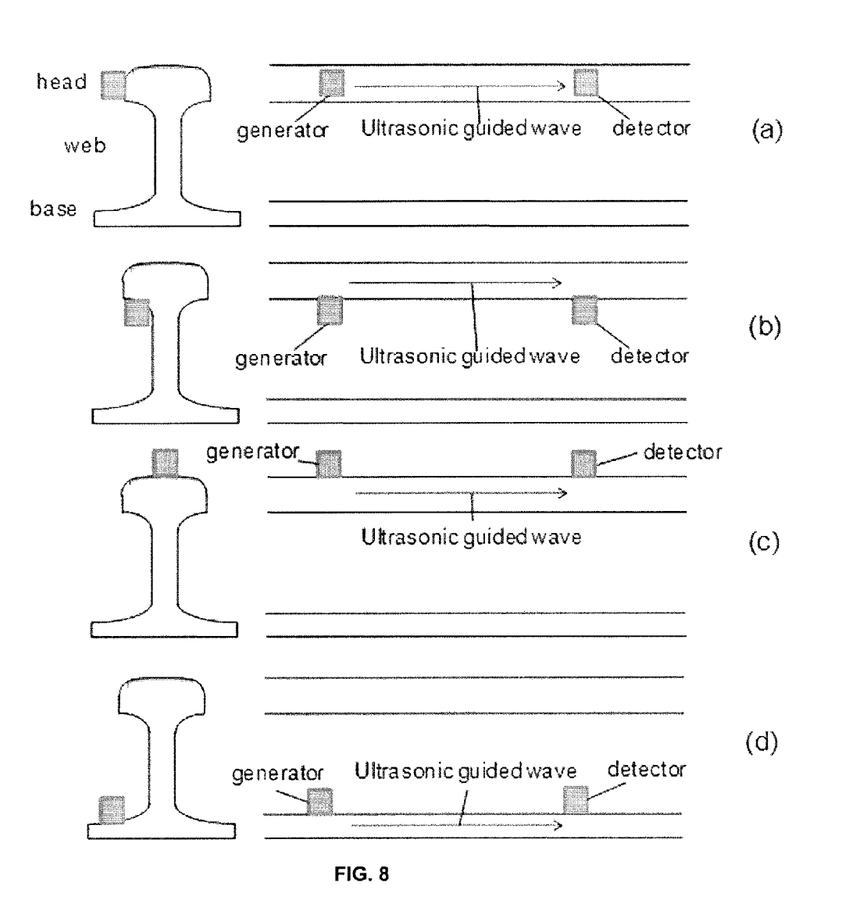
FIGS. 8-10 depict implementation examples.

In other possible implementations of neutral temperature measurement with ultrasonic guided waves, the ultrasonic generator and the ultrasonic detector may be positioned on the side of the railhead, under the railhead, at the top of the railhead, or on the rail base. These possible positions of the wave generator and detector are illustrated in FIG. 8, although other configurations of the generator and detectors may be implemented as well.

In another implementation, ultrasonic bulk waves, i.e. longitudinal or shear waves propagating in any direction of the solid (e.g., rail, pipeline, and the like) may be used.

Figure 9:
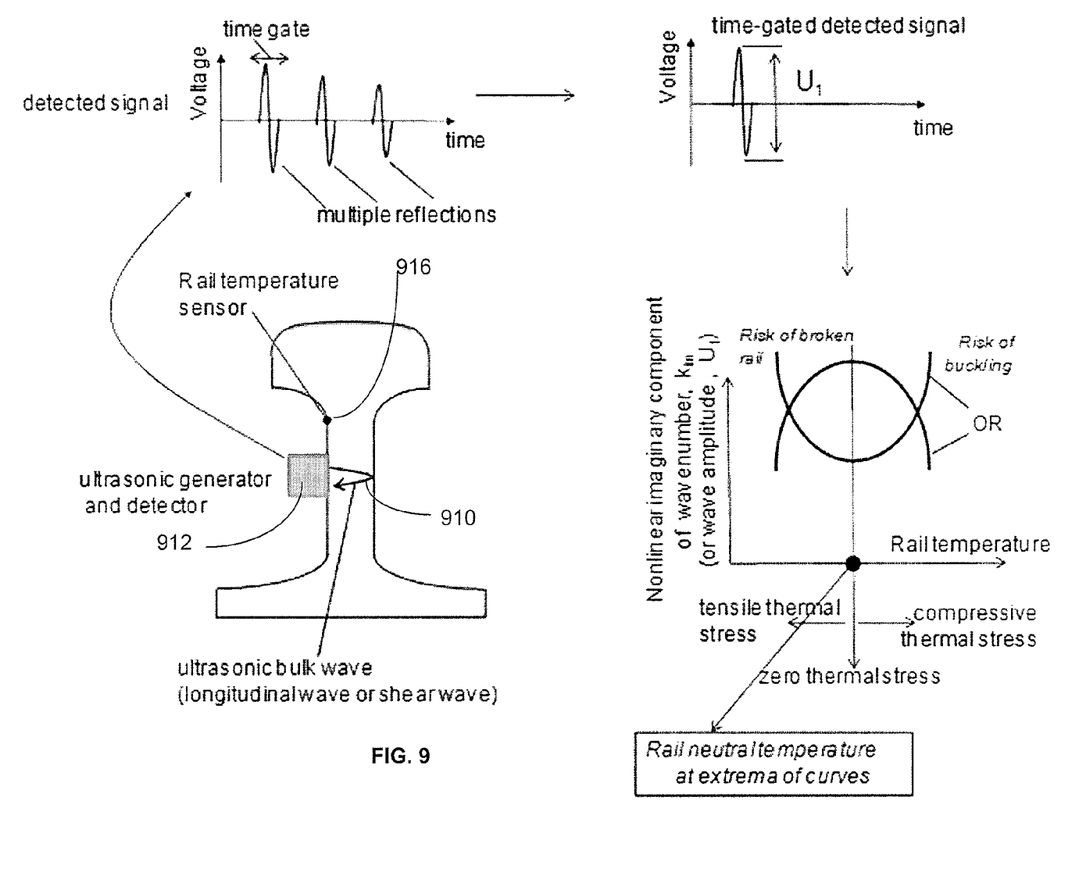

A schematic of a possible bulk wave 910 implementation for measuring the neutral temperature of a rail is shown in FIG. 9. An ultrasonic generator 912 (such as a piezoelectric transducer, although other generators are possible) may be attached to the rail web by way of an ultrasonic couplant (e.g. liquid or gel). The ultrasonic generator may induce in the rail ultrasonic bulk waves 910 (longitudinal or shear). The ultrasonic bulk waves may be reflected from the opposite surface of the rail web, and may be detected by the same ultrasonic transducer 912 that now acts as a detector. This may be considered a "pulse-echo" mode of ultrasonic testing, which is operated in a reflection mode.

A temperature sensor 916 may also used to measure the temperature of the rail, T. The temperature sensor may be one of a thermocouple, a non-contact infrared temperature sensor, or other types of temperature sensors.

Once the ultrasonic signal is detected, time gating may applied to isolate the specific wave reflection. Subsequently, the imaginary component of the wave number, $k_{im}$ (or the wave amplitude, U1) may be measured by one or more of the following features: a) root-mean square of the amplitude of the detected portion of the waves, b) variance of the amplitude of the detected portion of the waves, c) cross-correlation value of the amplitude of the detected portion of the waves, d) peak-to-peak value of the amplitude of the detected portion of the waves, e) peak value of the amplitude of the detected portion of the waves, f) Kurtosis value (e.g., a measure of the peakedness of the source signal, where a higher Kurtosis value implies more of the variance due to infrequent extreme deviations) of the amplitude of the detected portion of the waves, g) at least one other time-domain Statistical Moment corresponding to properties of the detected portion of the waves, h) at least one other frequency-domain Statistical Moment corresponding to the properties of the detected portion of the waves, and/or i) normalized values of any of feature values.

The imaginary component of the wave number, $k_{im}$, may then plotted as a function of the rail's temperature, T, as measured by the temperature sensor, for a period of time (e.g. 24 hours, although different times are possible). The rail's temperature T corresponding to an extrema value (e.g., a minimum value or a maximum value) of $k_{im}$ may thus represent the rail's neutral temperature, $T_N$.

Figure 10:
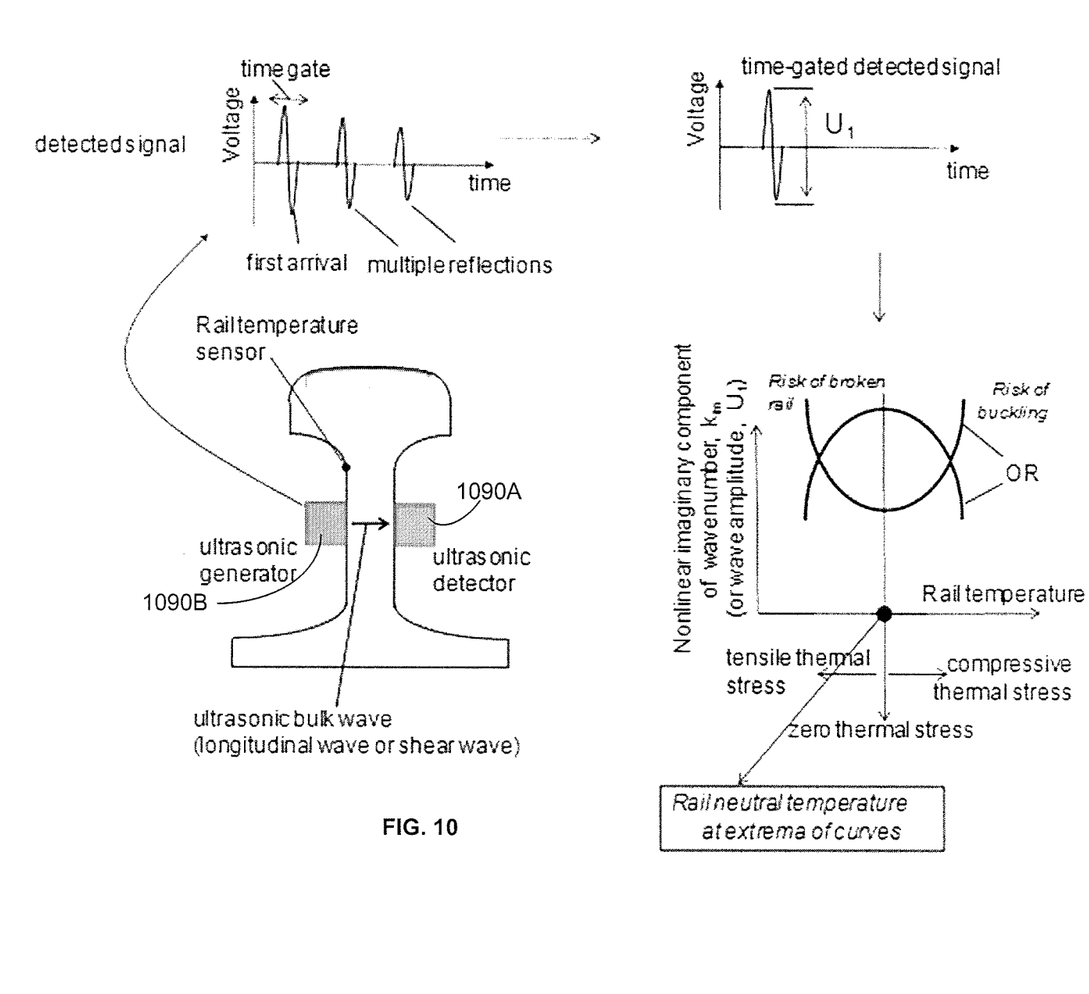

In other possible implementations with ultrasonic bulk waves, the ultrasonic generator and the ultrasonic detector may be positioned on opposite sides of the rail web, according to the classical "through-transmission" mode of ultrasonic testing as shown at FIG. 10. Referring to FIG. 10, at least one ultrasonic generator 1090B is placed on one side of the web and at least one ultrasonic detector 1090A is placed on the opposite side of the web.

For the ultrasonic bulk wave implementation depicted in FIG. 9 (reflection mode) and in FIG. 10 (transmission mode), the imaginary component of the wave number may be also measured in a similar manner as discussed with respect to FIG. 6 and Equation (5) by considering two successive wave reflections measured by the same ultrasonice detector. In this case, the distance $(x_2-x_1)$ in Equation (5) becomes the length of the path travelled by the wave between the two reflections (e.g., twice the thickness of the rail web). In addition, although the transducers shown in FIG. 9 and FIG. 10 are positioned on the rail web, other transducer positions may be employed, such as on the railhead or on the rail base. Moreover, other quantities of detectors and generators may be used as well.

Figure 11:
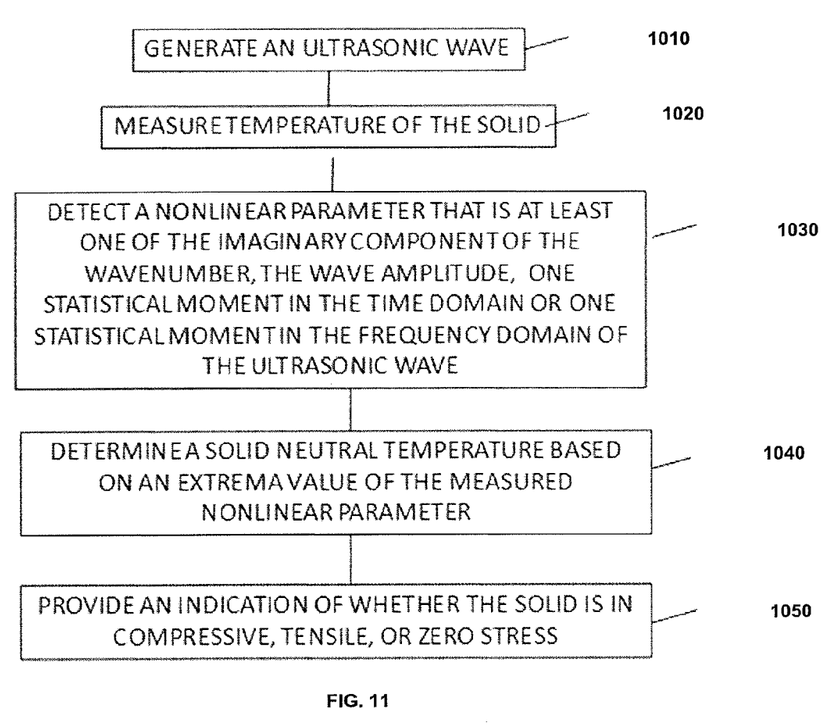
FIG. 11 depicts an example of a process.

FIG. 11 depicts a flowchart of a process for detecting the neutral temperature of a solid.

At 1010, an ultrasonic wave may be generated and then applied to an object, such as for example a rail, at an application point to cause resultant waves (e.g., ultrasonic waves) to travel, at least partly, through the rail. The energy may be applied by one or more generators, which may include contact type generators (e.g., piezoelectric transducers, impact hammers, ultrasonic wheels, ultrasonic sleds, water coupled generators, etc.), or non-contact generators (such as for example a laser acoustic system, air-coupled transducers, electromagnetic-acoustic transducer (EMAT), etc.).

At 1020, the temperature of the rail may be measured by for example, a temperature sensor, a thermocouple, and/or a non-contact infrared sensor.

At 1030, having caused waves to travel in the object (an object such as for example a rail), at least a portion of the waves traveling through the rail may be detected by one or more detectors. The detectors may be configured to detect, for example, ultrasonic waves, and may be controllably configured to detect particular types of waves, e.g., ultrasonic guided waves, ultrasonic Rayleigh waves, ultrasonic bulk waves, etc., by, for example, controlling the time window (also referred to as time gating) during which the detectors detect waves, as well as the wave generation angles. For example, the detector may detect at least the fundamental frequency component(s) of the ultrasonic wave, or other statistical moments in one of the time domain and the frequency domain.

At 1040, a rail neutral temperature may be determined based on the imaginary component of the wave number or the detected wave amplitude. For example, the detector and/or analyzer may perform a Fourier Transform, a Fast Fourier Transform, and/or other operation to extract the magnitude values of the fundamental frequency and of one or more of statistical moments in the time domain or in the frequency domain, at various rail temperatures. The extrema of the magnitude values of the fundamental frequency and/or of the statistical moments in the time domain or in the frequency domain may be used to determine the rail's neutral temperature.

At 1050, an indication of the rail's neutral temperature may be provided. For example, the analyzer may provide an indication, such as for example a message, alert, and the like to a user interface at a computer (or other processor) to alert a user (e.g., whether the rail is in compressive, tensile or zero stress).

The process of FIG. 11 may be implemented either at a fixed position of the rail or pipe for "wayside" stationary measurement, or in an "in-motion" system for continuous measurement at several positions along the rail or pipe.

In some example implementations, the ultrasonic generator and detector may be positioned in either a "through-transmission" lay-out (see, for example, FIG. 5, 6, 8 or 10) where the analysis is performed on the wave propagating from the generator to the detector that are two separate devices, or in a "pulse-echo" lay-out (see, for example, FIG. 9) where the analysis is performed on the wave generated by a generator, reflected by the solid's boundaries, and the reflection is detected by the same generator.

In some example implementations the measurements disclosed herein may be carried out using a single generator and two separate detectors (see, for example, FIG. 6), in which case the neutral temperature of the solid may be determined as an extrema value of the ratio of at least one of the imaginary component of the wavenumber, the wave amplitude, the wave strength, one statistical moment in the time domain or one statistical moment in the frequency domain of the ultrasonic waves received by the two detectors.

The systems and methods disclosed herein may be embodied in various forms including, for example, a data processor, such as for example a computer that also includes a storage, digital electronic circuitry, firmware, software, or in combinations of them. Moreover, the above-noted features and other aspects and principles of the present disclosed embodiments may be implemented in various environments. Such environments and related applications may be specially constructed for performing the various processes and operations according to the disclosed embodiments or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the disclosed embodiments, or it may be more convenient to construct a specialized apparatus or system to perform the required methods and techniques.

The systems and methods disclosed herein may be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

The foregoing description is intended to illustrate but not to limit the scope of the invention, which is defined by the scope of the appended claims. Other embodiments are within the scope of the following claims.

What is claimed:

1. A method comprising:
    generating, by an ultrasonic generator, at least one ultrasonic wave to enable the at least one ultrasonic wave to propagate through a rail, the at least one ultrasonic wave including an ultrasonic Rayleigh wave propagating along the surface of the rail;
    measuring, by a temperature sensor, a temperature of the rail;
    detecting, by a detector, the at least one ultrasonic wave including the ultrasonic Rayleigh wave propagating through the rail, the detector enabling detection of a wave strength;
    determining, based at least on the measured temperature and an extrema value of the wave strength, a neutral temperature of the rail, wherein the neutral temperature of the rail represents a corresponding temperature at which a thermal stress in the rail is about zero; and
    providing, to a user interface, the determined neutral temperature to provide an indication of whether the rail is in compressive stress, tensile stress, or zero stress.

2. The method of claim 1 further comprising:
    normalizing the wave strength in the frequency domain of the at least one ultrasonic wave.

3. The method of claim 1, wherein the at least one ultrasonic wave comprises an ultrasonic guided wave propagating along a predominant direction of the rail.

4. The method of claim 1, wherein the at least one ultrasonic wave comprises an ultrasonic longitudinal wave and/or an ultrasonic shear wave propagating in one or more directions in the rail.

5. An apparatus comprising:
    an ultrasonic generator configured to at least generate at least one ultrasonic wave to enable the at least one ultrasonic wave to propagate through a rail, the at least one ultrasonic wave including an ultrasonic Rayleigh wave propagating along the surface of the rail;
    a detector configured to at least detect the at least one ultrasonic wave including the ultrasonic Rayleigh wave propagating through the rail, the detector enabling detection of a wave strength; and
    at least one processor configured to at least
        determine, based at least on a measured temperature and an extrema value of the wave strength, a neutral temperature of the rail, wherein the neutral temperature of the rail represents a corresponding temperature at which a thermal stress in the rail is about zero, and
        provide, to a user interface, the determined neutral temperature to provide an indication of whether the rail is in compressive stress, tensile stress, or zero stress.

6. The apparatus of claim 5, wherein the at least one processor is further configured to at least normalize the wave strength in the frequency domain of the at least one ultrasonic wave.

7. The apparatus of claim 5, wherein the at least one ultrasonic wave comprises an ultrasonic guided wave propagating along a predominant direction of the rail.

8. The apparatus of claim 5, wherein the at least one ultrasonic wave comprises an ultrasonic longitudinal wave and/or an ultrasonic shear wave propagating in one or more directions in the rail.

9. A non-transitory computer-readable medium including computer code which when executed by at least one processor circuitry provides operations comprising:
    generating, by an ultrasonic generator, at least one ultrasonic wave to enable the at least one ultrasonic wave to propagate through a rail, the at least one ultrasonic wave including an ultrasonic Rayleigh wave propagating along the surface of the rail;
    measuring, by a temperature sensor, a temperature of the rail;
    detecting, by a detector, the at least one ultrasonic wave including the ultrasonic Rayleigh wave propagating through the rail, the detector enabling detection of a wave strength;
    determining, based at least on the measured temperature and an extrema value of the wave strength, a neutral temperature of the rail, wherein the neutral temperature of the rail represents a corresponding temperature at which a thermal stress in the rail is about zero; and
    providing, to a user interface, the determined neutral temperature to provide an indication of whether the rail is in compressive stress, tensile stress, or zero stress.

* * * * *